United States Patent
Hegel et al.

(10) Patent No.: US 8,475,519 B2
(45) Date of Patent: Jul. 2, 2013

(54) X-RAY VISIBILITY AND CORROSION RESISTANCE OF NITI STENTS USING MARKERS MADE OF SANDWICH MATERIAL

(75) Inventors: Alexander Hegel, Karlsruhe (DE); Rainer Steegmuller, Magstadt (DE); Bernd Schrader, Keltern (DE)

(73) Assignee: Admedes Schuessler GmbH, Pforzheim (DE)

( * ) Notice: Subject to any disclaimer, the term of this patent is extended or adjusted under 35 U.S.C. 154(b) by 1307 days.

(21) Appl. No.: 11/505,625

(22) Filed: Aug. 16, 2006

(65) Prior Publication Data

US 2007/0043429 A1 Feb. 22, 2007

(30) Foreign Application Priority Data

Aug. 18, 2005 (DE) .......................... 10 2005 039 136

(51) Int. Cl.
*A61F 2/06* (2006.01)
(52) U.S. Cl.
USPC .......................................................... 623/1.34
(58) Field of Classification Search
USPC ................ 623/11, 1, 12, 1.34, 1.1, 1.15
See application file for complete search history.

(56) References Cited

U.S. PATENT DOCUMENTS

| | | |
|---|---|---|
| 5,443,500 A | 8/1995 | Sigwart |
| 5,632,771 A | 5/1997 | Boatman et al. |
| 5,741,327 A | 4/1998 | Frantzen |
| 5,824,054 A | 10/1998 | Khosravi et al. |
| 5,861,027 A | 1/1999 | Trapp |
| 6,022,374 A | 2/2000 | Imran |
| 6,231,598 B1 | 5/2001 | Berry et al. |
| 6,293,966 B1 | 9/2001 | Frantzen |
| 6,334,871 B1 * | 1/2002 | Dor et al. ................. 623/1.34 |
| 6,402,777 B1 | 6/2002 | Globerman et al. |
| 6,409,752 B1 | 6/2002 | Boatman et al. |
| 6,464,720 B2 | 10/2002 | Boatman et al. |
| 6,730,116 B1 | 5/2004 | Wolinsky et al. |
| 6,863,685 B2 | 3/2005 | Davila et al. |
| 6,918,928 B2 | 7/2005 | Wolinsky et al. |
| 2002/0193867 A1 | 12/2002 | Gladdish, Jr. et al. |
| 2002/0193869 A1 | 12/2002 | Dang |

(Continued)

FOREIGN PATENT DOCUMENTS

| | | |
|---|---|---|
| DE | 100 64 596 A1 | 12/2000 |
| DE | 102 35 868 A1 | 7/2002 |

(Continued)

OTHER PUBLICATIONS

Schumacher, M., "Diagnostic Workup in Cerebral Aneurysms," *Cerebral Aneurysms*, pp. 13-24, Nakstadt PHj (ed), Bologna, Centauro (2000).

*Primary Examiner* — Elmer Chao
(74) *Attorney, Agent, or Firm* — Kilpatrick Townsend & Stockton LLP (57) ABSTRACT

A bodily implant, in particular a stent, for insertion or implantation into a living body, having a marker element for increasing X-ray visibility, which is at least partially insertable into a cut-out in an implant structure and which has a coated material comprising at least two layers. A corresponding method for manufacturing a marker element from a coated material, and a corresponding method for manufacturing a bodily implant, in particular a stent, having a marker element which is visible to X-rays, is disclosed.

41 Claims, 9 Drawing Sheets

U.S. PATENT DOCUMENTS

| | | |
|---|---|---|
| 2003/0060872 A1* | 3/2003 | Gomringer et al. .......... 623/1.15 |
| 2003/0106218 A1 | 6/2003 | Jalisi et al. |
| 2003/0114912 A1 | 6/2003 | Sequin et al. |
| 2004/0088038 A1 | 5/2004 | Dehnad et al. |
| 2004/0088039 A1 | 5/2004 | Lee et al. |
| 2004/0236407 A1 | 11/2004 | Fierens et al. |
| 2005/0060025 A1* | 3/2005 | Mackiewicz et al. ........ 623/1.34 |
| 2005/0172471 A1 | 8/2005 | Vietmeier |
| 2005/0256564 A1 | 11/2005 | Yang et al. |
| 2006/0085059 A1 | 4/2006 | Ehrlinspiel et al. |
| 2006/0217799 A1 | 9/2006 | Mailander et al. |
| 2006/0259129 A1 | 11/2006 | Hegel |
| 2007/0027552 A1 | 2/2007 | Farnsworth et al. |

FOREIGN PATENT DOCUMENTS

| | | |
|---|---|---|
| DE | 103 23 475 A1 | 12/2004 |
| DE | 04 014 789 | 3/2005 |
| EP | 0 737 452 A1 | 10/1996 |
| EP | 0 800 800 A1 | 10/1997 |
| EP | 0 801 933 A1 | 10/1997 |
| EP | 0 938 879 A2 | 9/1999 |
| EP | 0 997 116 A2 | 5/2000 |
| EP | 0 891 166 B1 | 1/2005 |
| EP | 1 523 959 A2 | 4/2005 |
| WO | WO 95/01761 A2 | 1/1995 |
| WO | 98/31304 A1 | 7/1998 |
| WO | WO 99/02092 A1 | 1/1999 |
| WO | WO 99/15108 A2 | 4/1999 |
| WO | WO 02/24247 A1 | 3/2002 |
| WO | WO 03/101343 A1 | 12/2003 |
| WO | WO 2004/02368 A1 | 1/2004 |

* cited by examiner

X-RAY VISIBILITY AND CORROSION RESISTANCE OF NITI STENTS USING MARKERS MADE OF SANDWICH MATERIAL

CROSS-REFERENCES TO RELATED APPLICATIONS

The present application claims priority to German Application No. 10-2005-039136.2, filed Aug. 18, 2005, which are incorporated herein by reference.

BACKGROUND OF THE INVENTION

The present invention relates to a bodily implant, in particular a stent, for insertion into a living body, having good X-ray visibility, and a method for manufacturing a marker element for increasing the X-ray visibility, and a method for manufacturing a bodily implant.

Bodily implants or stents of this type protect channels in living bodies, such as blood vessels, the esophagus, the urethra, or renal passages, for example, by insertion of the stent and expansion of same inside the bodily channel. In this manner collapse or occlusion of the particular bodily channel may be prevented. A stent is also used, for example, for intercerebral aneurysms, which are the most common cause of non-traumatic subarachnoid hemorrhages. The incidence occurs in 1% of the general population, and, according to autopsy studies, as high as 9%. From a pathomorphological standpoint, intracerebral aneurysms as a rule are genuine saccular aneurysms which are usually localized in vascular arborizations (see, for example, Schumacher, M., "Diagnostic workup in cerebral aneurysms" in Nakstadt PHj (ed.): "Cerebral Aneurysms," pp. 13-24, Bologna: Centauro (2000)).

Such bodily implants or stents may also be used as carriers for medications to enable local therapy within the bodily channel. These stents are inserted in a collapsed state into a bodily channel, and are expanded after being positioned in the bodily channel. The stents are usually composed of stainless steel or a cobalt-chromium-tantalum alloy. The stents may be inserted into the bodily channel by means of an expansion device, a balloon catheter, for example, and are expanded there.

However, the stents may also be composed of other materials, for example polymers, self-degradable materials such as lactic acid materials or derivatives thereof, in addition to nitinol (nickel-titanium alloys) and/or other self-expanding materials such as so-called shape memory materials. To increase the X-ray visibility of these stents, the stents are often provided with additional elements (known as markers) which are produced from a material having high X-ray visibility.

Gold or a gold alloy is a particularly suitable material for the markers, since gold has very good X-ray visibility. Markers are also produced from tantalum, but its X-ray visibility is not as satisfactory as that of gold. However, gold has the disadvantage that it is less resistant to corrosion than tantalum.

BRIEF SUMMARY OF THE INVENTION

The present invention provides a bodily implant having high X-ray visibility and high corrosion resistance, a method for manufacturing a marker element having high X-ray visibility and high corrosion resistance, and a method for manufacturing a bodily implant having high X-ray visibility and high corrosion resistance.

In one embodiment of the present invention, a bodily implant, in particular a stent, is provided for insertion or implantation into a living body, the bodily implant having a marker element for increasing the X-ray visibility which may be at least partially inserted into a cut-out in an implant structure and which has a coated material comprising at least two layers.

Due to the fact that the marker element has a coated material, use may be made of the advantageous properties of two marker materials, such as gold and tantalum, for example. In this manner a material, for example gold with high X ray visibility, is protected by a material, for example tantalum, from blood or blood components by virtue of its high corrosion resistance, and/or is protected from fluid-dynamic ablation by virtue of its high resistance. As the result of the encapsulation or layering of the material having lower corrosion resistance with a material having high corrosion resistance, the material having low corrosion resistance is protected from corrosion by the fact that the material having low corrosion resistance is prevented from making contact with the stent material and/or with the bloodstream in the bodily vessel or cavity. The encapsulation or layering with the material having high corrosion resistance does not significantly affect the good X-ray visibility; i.e., the X-ray visibility is reduced by less than approximately 10% by the encapsulation or layering. The material with high X-ray visibility has a lower permeability to X-rays or other particles or high-energy radiation, i.e., in particular has a permeability (dB) compared to the stent material in the range of approximately 10 to 40% of the permeability (dB) value for the stent material.

In some embodiments, the marker element of the bodily implant has an eternally exposed area essentially resistant to corrosion. Contact of the less corrosion-resistant material with the stent material and/or with the bloodstream in the bodily vessel or cavity is reduced or avoided by protecting, at least in places, an inner layer composed of a less corrosion-resistant material by means of at least one outer layer composed of a corrosion-resistant material.

In some embodiments, the coated material of the marker element has two outer layers and at least one intermediate inner layer, the outer layers comprising an essentially corrosion-resistant material and the inner layer comprising a material with good X-ray visibility.

In one embodiment of the present invention, the bodily implant comprises a cut-out (eyelet) that is open on both sides. Contact of the less corrosion-resistant material with the stent material and/or with the bloodstream in the bodily vessel or cavity is avoided by protecting an inner layer composed of a less corrosion-resistant material by means of at least two outer layers composed of a corrosion-resistant material.

The marker element may be designed as a rivet which has an essentially cylindrical shape and which is at least partially insertable into a corresponding cut-out in the bodily implant. The marker element designed as a rivet may be pressed and/or is welded, using a laser, into the cut-out in the bodily implant.

By designing the marker element as a rivet, the marker element may be inserted into a corresponding cut-out in the stent by use of a simple method, and is either pressed and/or welded using a laser to fix the marker element in place in the cut-out in the stent.

An inner layer of the coated material may be encapsulated in such a way that the inner layer has no contact with the material of the bodily implant and/or no contact with the bloodstream in the bodily vessel. The inner layer may include gold or a gold alloy, and the outer layer may include tantalum and/or nitinol.

By producing the inner layer from gold or a gold alloy, the marker element and the stent provided with this marker element has an improved X-ray visibility, while at the same time corrosion of the gold is prevented because the gold layer has no contact with the stent material and/or with the bloodstream in the bodily vessel.

By producing the outer layer from tantalum or nitinol, this layer has corrosion resistance, and at the same time also has relatively high X ray visibility. The outer layer may be produced from the same material as that of the stent itself, as the result of which the stent acquires a homogeneous appearance and has uniform corrosion resistance and biocompatibility over the entire stent surface. In addition, such a marker element can be welded to the stent material and then essentially polished.

In one embodiment of the present invention, a method for manufacturing a marker element from a coated material is also provided, comprising: manufacture of a coated panel from a plurality of flat materials by rolling, welding, gluing, and/or by an electroplating process; and manufacture of a marker element from the coated panel by punching, laser cutting, and/or water cutting.

The marker element may be easily manufactured by cutting it out from an appropriate sandwich material or a coated material/panel. For this purpose a rivet blank may be produced which already has the outer and inner layers. This rivet blank may be shaped into a precisely fitting rivet in a subsequent shaping process.

In one embodiment of the present invention, a method for manufacturing a cylindrical marker element from a coated material is also provided, comprising: manufacture of a coated tube by drawing of a multilayer tube blank; and/or placement of tubes inside one another and joining the tubes by gluing, welding, and/or drawing.

Manufacturing the rivets from a coated material in the form of a coated tube or sandwich tube provides a simple method for manufacturing arched rivets for use in cylindrical stents. Such arched rivets have a slightly conical shape, which may be easily produced by cutting out a circular segment from a sandwich tube. The marker element may be shaped into a rivet in a subsequent shaping process.

According to one embodiment of the present invention, a method for manufacturing a bodily implant, in particular a stent, having a marker element that is visible to X-rays is also provided, comprising: forming a cut-out in an implant structure; forming a marker element from a coated material by use of one of the previously described methods; and pressing or riveting the marker element into the cut-out in the implant structure.

In some embodiments, the marker element is to be additionally welded in the cut-out by use of a laser. An outer layer of the coated material may be formed from the same material as that of the implant structure, and the marker element is polished after insertion.

BRIEF DESCRIPTION OF THE DRAWINGS

The present invention is explained in greater detail below, with reference to exemplary embodiments in conjunction with the appended drawings.

DETAILED DESCRIPTION OF THE INVENTION

Figure 1:
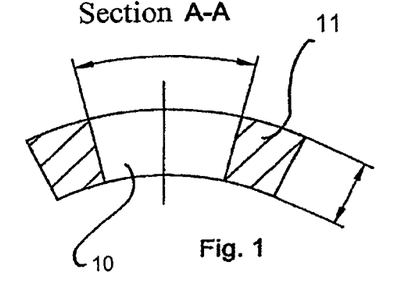
FIGS. 1 through 3 show a cut-out in a stent for insertion of a marker element in accordance with an embodiment of the present invention, the cut-out having a slightly conical shape on account of the cylindrical shape of the stent.
Figure 2:
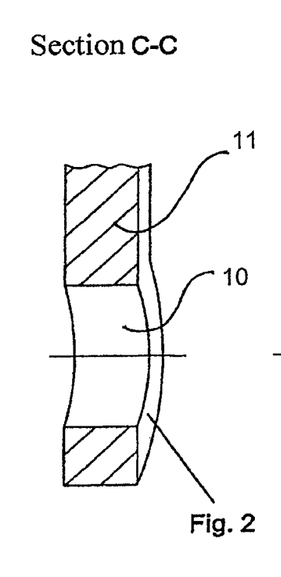
Figure 3:
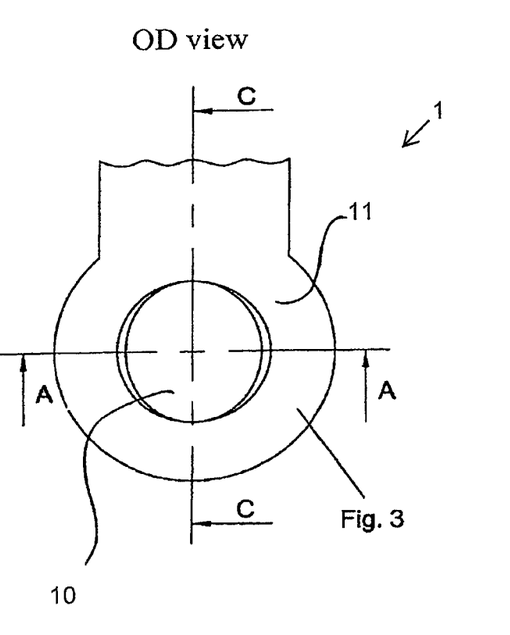

As shown in FIGS. 1 through 3, a stent structure 11 for a bodily implant 1 is provided with a cut-out 10 for insertion of a marker element 2. FIGS. 1 through 3 show a cylindrical stent 1 having a slightly conical cut-out 10 (eyelet). A marker element 2 which is insertable into this conical cut-out 10 may comprise a corresponding conical rivet.

Figure 4:
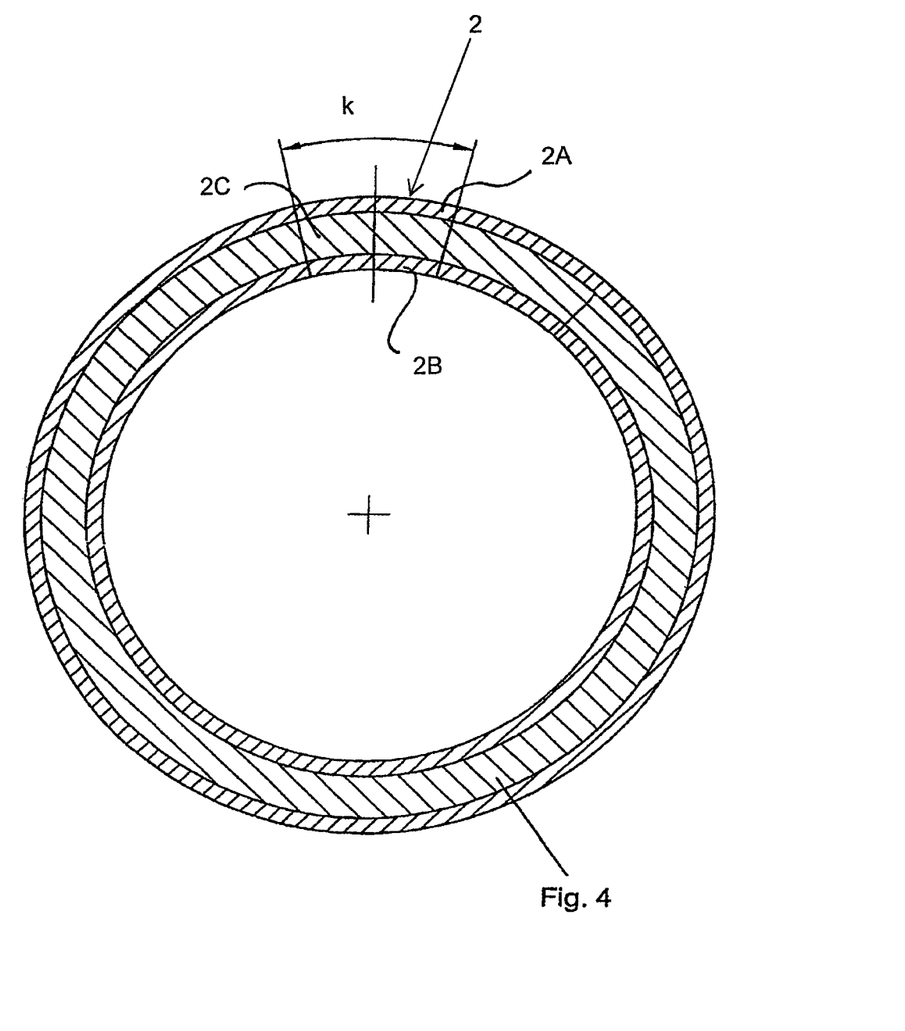
FIG. 4 shows a sandwich material for manufacturing a marker element as a sandwich tube in accordance with an embodiment of the present invention.

Such an essentially conical rivet as a marker element 2 may be produced by drawing a coated material or sandwich material in tubular form from a multilayer tube blank by placing finished tubes inside one another and joining them by gluing, welding, and/or drawing by means of a drawing process, as shown in FIG. 4. In some embodiments, this tube shown in FIG. 4 has a layered, i.e., sandwich, structure having three layers 2A, 2B, and 2C. The middle or inner layer 2C (i.e., at least one of the inner layers) is produced from a material having high X-ray visibility, i.e., particularly low permeability (dB) for X-rays in the range of approximately 10% to 40% of the permeability of the stent material, but has a lower corrosion resistance and/or lower resistance to fluid-dynamic ablation or wear, such as gold or a gold alloy, for example, and the outer layers 2A, 2B are produced from a material having high corrosion resistance to blood or blood components, and/or having a high resistance to fluid-dynamic ablation, such as tantalum or nitinol, for example.

A conical marker element is produced from this at least partially coated tube or sandwich tube by cutting out or removal of a preferably essentially circular segment, i.e., circular segment K, as shown in FIG. 4. In some embodiments, this circular segment K of the crude marker element 2 has an essentially cylindrical shape or an essentially slightly conical shape.

Figure 5:
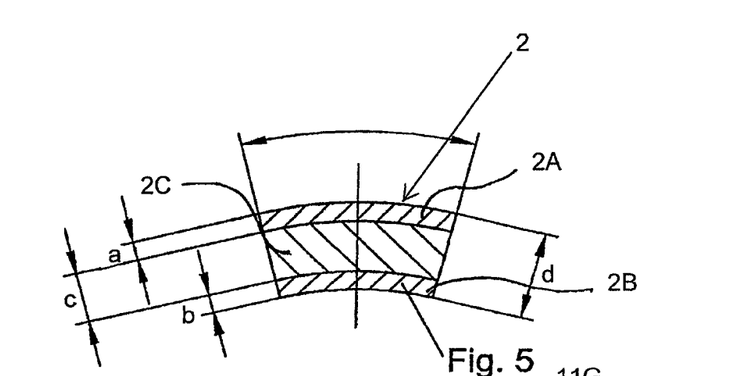
FIG. 5 shows a circular segment cut out of a sandwich tube in accordance with an embodiment of the present invention.
Figures 6, 7:
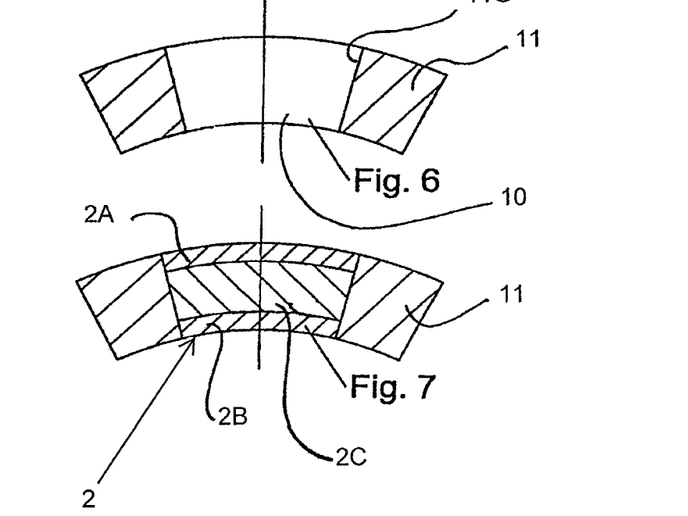
FIG. 6 shows a corresponding cut-out in a stent for insertion of a marker element as illustrated in FIG. 5.
FIG. 7 shows a marker element as illustrated in FIG. 5, which is inserted into the cut-out in the stent structure as illustrated in FIG. 6.

FIG. 5 shows a cross section of the marker element 2 cut out, punched, or removed from the sandwich tube. In one embodiment of the present invention, this marker element has outer layers 2A and 2B and at least one inner layer 2C. The outer layers 2A and 2B have a layer thickness a and b, respectively, and the inner layer 2C has a layer thickness c, the overall thickness being designated by d (d=a+b+c). FIG. 6 shows a cut-out 10 in a stent structure 11 in which a marker element 2 as illustrated in FIG. 5 may be at least partially inserted. The marker element 2 may be at least partially inserted into the stent structure 11 with a locking and/or positive fit.

Figure 25:
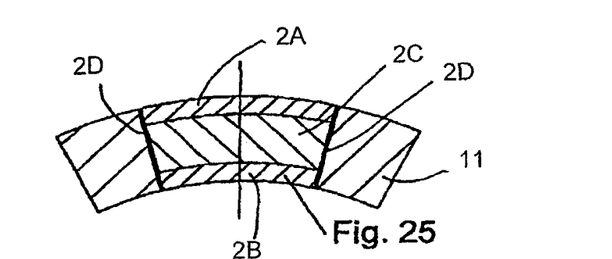
FIG. 25 shows a marker element having a conical shape, with an additional protective layer, in accordance with an embodiment of the present invention.
Figure 26:
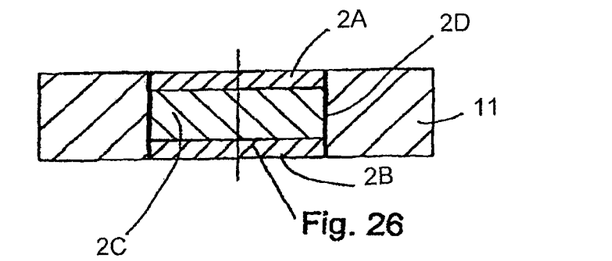
FIG. 26 shows a marker element having a cylindrical shape, with an additional protective layer, in accordance with an embodiment of the present invention.

FIG. 7 shows the marker element 2 after insertion into the stent structure 11. The marker element 2 as illustrated in FIG. 5 may be cut out or punched from a sandwich tube as illustrated in FIG. 4 by means of a punching process, laser, and/or a water cutting process. The advantage of such a marker element is a high-precision fit of the rivet with respect to the cut-out 10 in the stent structure 11, and high X-ray visibility with a simultaneously low susceptibility to corrosion, since as a result of the encapsulation or layering the material with high X-ray visibility has essentially no contact with the stent material and/or with the bloodstream in the bodily vessel. In particular, in the encapsulation the inner material 2C having the higher X-ray visibility is separated from the stent structure 11 by a protective layer 2D (shown in FIGS. 25 and 26) which is provided or placed essentially between the inner material 2C having higher X-ray visibility and an interface 11G of the stent structure 11, so that likewise little or no corrosion (resulting from an electrochemical reaction, for example) can occur in this region. Furthermore, the layer between the inner material having higher X ray visibility and an interface 11G of the stent structure 11 can likewise ensure that, if there is not a perfect locking fit between the marker element 2 and the stent structure 11 (for example, if there is a small gap between them), no bodily fluid can come into contact with the inner material having higher X-ray visibility.

Figure 7A:
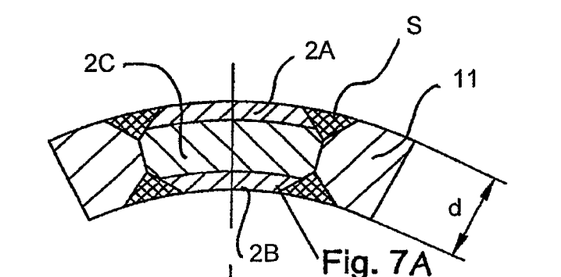
FIG. 7A shows the welding of the marker element after insertion in accordance with an embodiment of the present invention.

In addition, the marker element 2 may be welded to the stent structure 11, as shown in FIG. 7A. The marker element 2 is welded at its outer and inner circumference to the stent structure 11 by means of a weld seam S.

Figure 8:
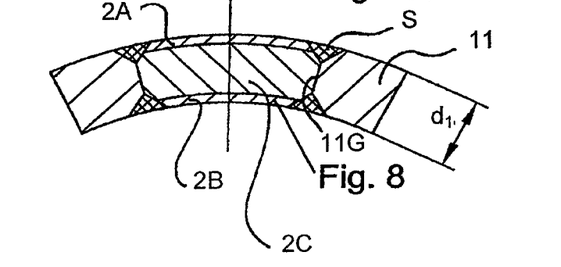
FIG. 8 shows the stent structure with the inserted marker element after polishing in accordance with an embodiment of the present invention.

To achieve a homogeneous appearance, i.e., good usability, of the stent, the stent structure 11 having the inserted marker element 2 and the weld seams S in the region of the eyelet may be polished, thereby reducing the thickness d to a thickness d1 as shown in FIGS. 7A and 8. As a result of the weld seam S the inner layer 2C of the marker element 2 is at least partially, preferably essentially completely, encapsulated, so that the inner layer 2C has no contact with the stent material and/or with the bloodstream in the bodily vessel or cavity, thus preventing corrosion of the inner layer 2C.

Figure 9:
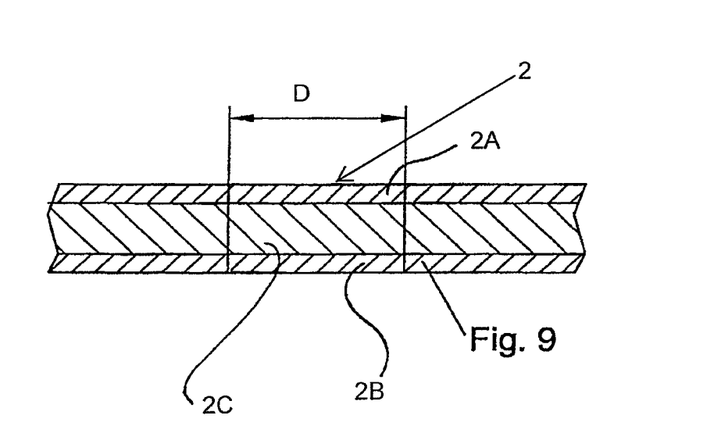
FIG. 9 shows a sandwich plate for manufacture of a cylindrical marker element in accordance with an embodiment of the present invention.
Figure 10:
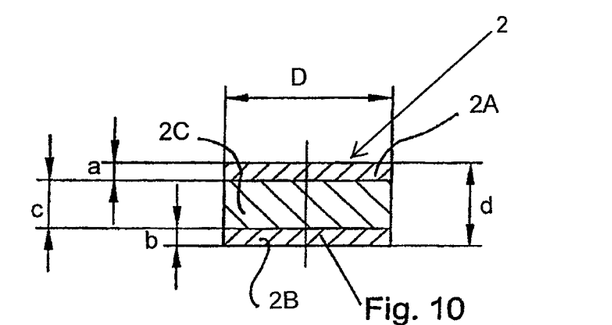
FIG. 10 shows a marker element, punched or cut out of a sandwich plate, in the shape of a cylindrical rivet in accordance with an embodiment of the present invention.
Figure 11:
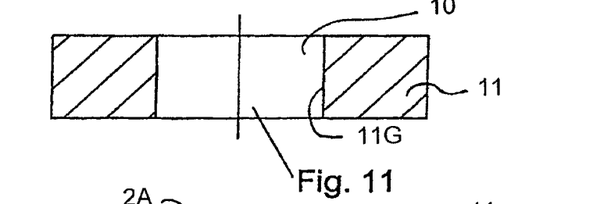
FIG. 11 shows a corresponding cylindrical cut-out in a stent structure for insertion of a marker element, as illustrated in FIG. 10.
Figure 12:
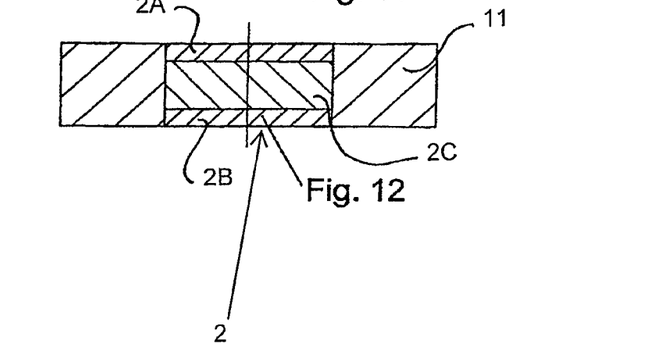
FIG. 12 shows a stent structure having a marker element, made of a sandwich material, inserted into the marker element, in accordance with an embodiment of the present invention.

FIGS. 9 through 14 show another embodiment of the present invention. As shown in FIG. 9, a coated material or sandwich material may be produced in plate form, for example by rolling, welding, or gluing and/or by another technical method. Alternatively or additionally, a sandwich panel, i.e., an arrangement having a layered structure, may also be produced, at least partially, by an electroplating process. Crude rivets are then cut out from this sandwich panel by means of a punching process, laser process, or water cutting process, as shown in FIGS. 9 and 10. This crude rivet has a cylindrical shape and is insertable into a cut-out 10 in a stent structure 11, as shown in FIG. 11. FIG. 12 shows the stent structure 11 with the marker element 2, having outer layers 2A, 2B, and an inner layer 2C, inserted in stent structure 11.

Figure 13:
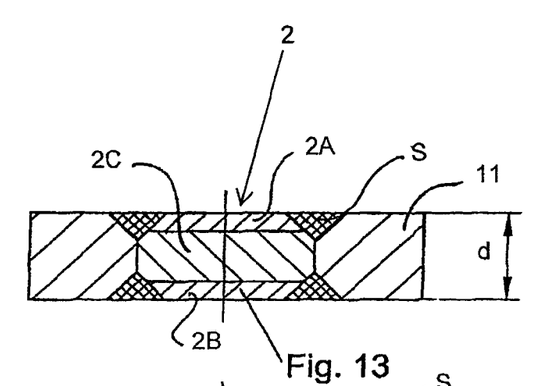
FIG. 13 shows the stent structure with the cylindrical marker element inserted into the stent structure, after welding, in accordance with an embodiment of present invention.
Figure 14:
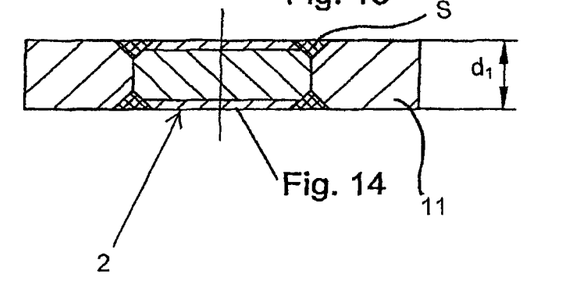
FIG. 14 shows the stent structure with the marker element inserted into the stent structure, after welding and polishing, in accordance with an embodiment of the present invention.
Figure 15:
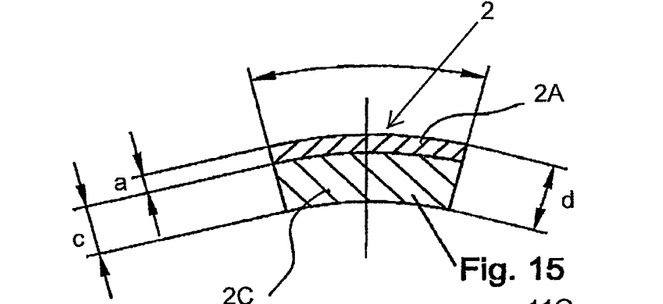
FIG. 15 shows a two-layer circular segment cut out from a sandwich tube in accordance with an embodiment of the present invention.
Figure 16:
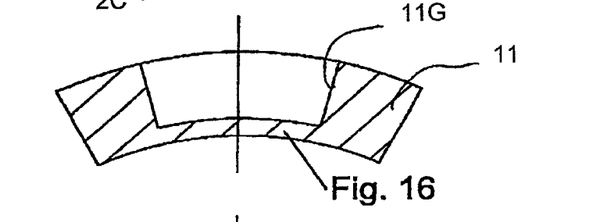
FIG. 16 shows a corresponding cut-out of a stent for insertion of a marker element, as illustrated in FIG. 15.
Figure 17:
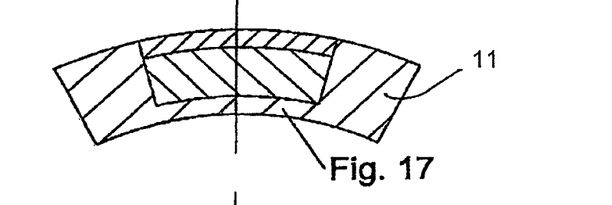
FIG. 17 shows a marker element as illustrated in FIG. 15, which is inserted into the cut-out in the stent structure as illustrated in FIG. 16.
Figure 18:
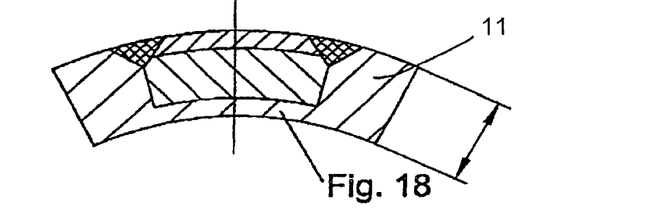
FIG. 18 shows the welding of the marker element after insertion in accordance with an embodiment of the present invention.
Figure 19:
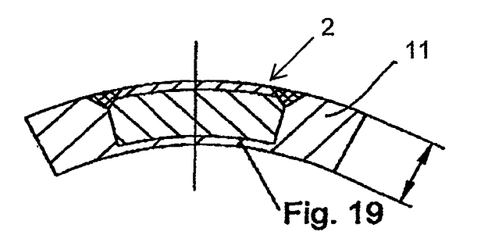
FIG. 19 shows the stent structure with the inserted marker element, after polishing, in accordance with an embodiment of the present invention.
Figure 20:
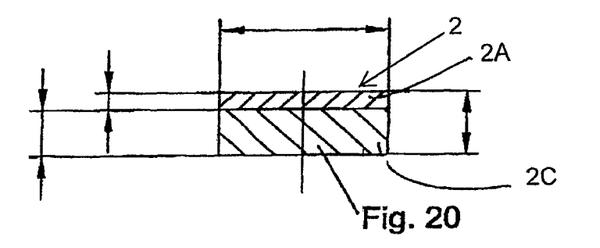
FIG. 20 shows a two-layer marker element, punched or cut out of a sandwich plate, in the shape of a cylindrical rivet, in accordance with an embodiment of the present invention.
Figure 21:
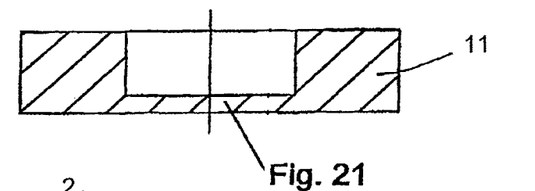
FIG. 21 shows a corresponding cylindrical cut-out in a stent structure for insertion of a marker element, as illustrated in FIG. 20.
Figure 22:
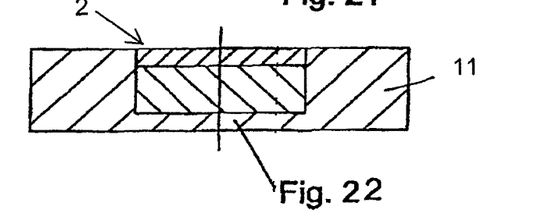
FIG. 22 shows a stent structure having a marker element, made of a sandwich material, inserted into the stent structure, in accordance with an embodiment of the present invention.
Figure 23:
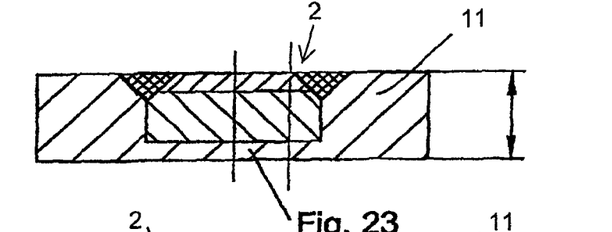
FIG. 23 shows the stent structure with the cylindrical marker element inserted into the stent structure, after welding, in accordance with an embodiment of the present invention.
Figure 24:
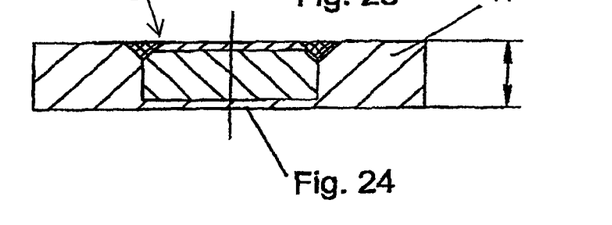
FIG. 24 shows the stent structure with the marker element inserted into the stent structure, after welding and polishing, in accordance with an embodiment of the present invention.

In some embodiments, this marker element 2 may be welded at its circumference to the stent structure 11 by means of a circular weld seam S, as shown in FIG. 13. In addition, the marker element together with the stent structure 11 and weld seam S may be polished, thereby reducing the thickness of the stent structure 11 from d to d1, as shown in FIG. 14.

To further increase the accuracy of fit of the rivet for the marker element 2 after the punching or cut-out process from the sandwich panel or layered structure shown in FIG. 9, this crude rivet 2 may undergo a subsequent shaping process such as cold pressing, forging, etc. However, the shape of the marker element 2 is not limited to the cylindrical shape, or the slightly conical shape. The rivet blank produced from the sandwich material may also be shaped into a double cone in a subsequent shaping process in order to achieve a locking fit in the cut-out 10 (eyelet) in the stent structure 11. With regard to this double cone shape, reference is made to U.S. patent application Ser. No. 11/412,689, filed on Apr. 26, 2006, which is incorporated by reference. In this case, as described in U.S. patent application Ser. No. 11/412,689, an essentially cylindrical marker element may be inserted into a cut-out 10 in a double cone shape and pressed into it, so that the marker element 2 has a double cone shape after the pressing. Welding of the marker element 2 may thus be omitted. As an alternative, however, the welding may be additionally performed, so that in particular a good seal is achieved for the intermediate layer with respect to the stent structure 11 and the blood in the bodily vessel.

The material of the sandwich marker 10 is not limited to the materials described herein; platinum, a platinum alloy, platinum-iridium, or niobium, for example, may also be used instead. Welding of the marker element 2 in the cut-out 10 may be performed using a laser. In some embodiments, the outer layers 2A and 2B are made from the same material as the stent structure 11, whereby as the result of polishing the stent acquires a particularly homogeneous appearance, i.e., good use characteristics, when inserted into the bodily vessel or cavity.

In addition, the coated material of the marker element 2 may have only two layers 2A, 2C. In this case, encapsulation or layering, at least in places, of layer 2C having lower corrosion resistance is achieved by placing the marker element 2 in a blind hole or recess in the stent structure 11, as shown in FIGS. 15 through 24. In other words, a two-layer marker element 2 is placed in a recess in the stent structure 11 in such a way that contact of layer 2C, having lower corrosion resistance, with blood or blood components is prevented by essentially covering with layer 2A having high corrosion resistance.

In embodiments described, it is particularly advantageous for essentially the entire stent as such, and not just the ends thereof, to be visible during an X-ray test, when multiple marker elements 2 are distributed over the stent structure 11. Thus, in the preferred stent the exact length and shape can be discerned within a bodily channel.

For this reason, in one embodiment of the present invention, the flexible wall structure is designed with bars and/or bar connectors, and the marker element 2 is attached to at least one of the bars or bar connectors.

In some embodiments, it is also advantageous when the bar or bar connector to which the marker element 2 is attached is provided with a correspondingly enlarged base. The enlarged base simplifies attachment of the marker element 2, and in itself also provides shielding from X-ray radiation.

The marker element 2 may also be provided in the interior, i.e., on the flexible wall structure, in at least one recess 10 or cavity. The marker element 2 may thus be embedded in the wall structure so that the flexible characteristic of the wall structure is not altered by the inserted marker element 2. Therefore it is not absolutely necessary to redesign the wall structure; instead, known and proven structures may advantageously be used.

In one embodiment of the present invention, the at least one recess 10 advantageously has a punctiform or linear shape. The points or lines may be provided on the bar connectors and/or on the bars. The bar connectors and bars are thus individually visible, so that particularly satisfactory conclusions can be drawn concerning the shape and configuration of an inserted stent.

Furthermore, the at least one recess 10 is advantageously designed as a cavity or passage opening. The marker element 2 may be inserted into such a recess or passage opening in a particularly durable manner.

The at least one recess 10 may be provided by configuring the raw material of the essentially cylindrical or tubular wall, and the marker element 2 is then inserted into the recess in such a way that, after the openings are subsequently provided for the flexible wall structure, sections of the marker element 2 remain inside the flexible wall structure. In this manner, the assembly effort for attaching the marker element 2 may be kept relatively low.

In this procedure, the at least one recess 10 may be designed, at least in places, as a groove in the circumferential direction, in the axial direction, and/or spirally, i.e., wound, on the raw material of the essentially tubular wall. For a stent manufactured in this manner, the marker element 2 is uniformly distributed over the entire stent wall, and at the same the assembly effort required is relatively low.

The at least one recess 10 may be provided in a particularly economical manner by laser cutting, laser ablation technology, mechanical grinding, milling, and/or erosion. The surface of the marker element 2 may be substantially flush with the surface of the essentially tubular wall structure. The exterior shape of such a stent corresponds to that of known stents, so that no additional problems result when the stent is inserted and configured in a bodily channel.

The marker element 2 may also be designed in a particularly simple manner as a rod or flat strip. It has been determined that particularly advantageous sizes for the points or lines in the marker element 2 attached according to the invention are diameters, widths, or thicknesses of approximately 10 μm to 200 μm. The flexible wall structure of the stent according to the invention may be made of nitinol or a nitinol alloy. The marker element 2 may include tantalum, niobium, gold, platinum, tungsten, or an alloy thereof.

Although the invention has been described with respect to specific embodiments, it will be appreciated that the invention is intended to cover all modifications and equivalents within the scope of the following claims.

What is claimed is:

1. A bodily implant for insertion into a living body, the bodily implant comprising:
   an implant structure having a cut-out formed therein; and
   a marker element to increase the X-ray visibility which is at least partially insertable into the cut-out in the implant structure,
   wherein the marker element has a coated material comprising at least two layers that are each made of a material that is different than that of the implant structure and that are each tapered such that the marker element is cone-shaped, and
   wherein the first layer and the second layer each have side surfaces that contact the implant structure, the first layer and the second layer each have top and bottom surfaces, and the entire side surfaces of the first layer and the second layer are each tapered along a plane extending from the top surface of the second layer to the bottom surface of the first layer.

2. The bodily implant according to claim 1, further comprising an externally exposed area, wherein the at least two layers are part of the externally exposed area and are resistant to corrosion.

3. The bodily implant according to claim 1, wherein the coated material of the marker element has two outer layers and at least one inner layer between them, the outer layers comprising a corrosion-resistant material and the inner layer comprising a material with good X-ray visibility.

4. The bodily implant according to claim 1, wherein the marker element is designed as a rivet which is at least partially insertable into a corresponding cut-out in the bodily implant.

5. The bodily implant according to claim 4, wherein the marker element designed as a rivet is pressed or is welded using a laser, or both, into the cut-out in the bodily implant.

6. The bodily implant according to claim 1, wherein an inner layer of the coated material is encapsulated in such a way that the inner layer has no contact with the material of the bodily implant or no contact with the bloodstream in the bodily vessel, or both.

7. The bodily implant according to claim 3, wherein the inner layer includes gold or a gold alloy.

8. The bodily implant according to claim 3, wherein the outer layers include tantalum or nitinol, or both.

9. The bodily implant according to claim 1, wherein the bodily implant is a stent.

10. The bodily implant according to claim 3, wherein the two outer layers are formed independent of the at least one inner layer.

11. The bodily implant according to claim 3, wherein each of the two outer layers and the at least one inner layer has tapered edges such that the marker element is cone-shaped.

12. The bodily implant according to claim 3, further comprising a protective layer provided between the at least one inner layer and an interface with the bodily implant.

13. The bodily implant according to claim 12, wherein the protective layer functions to reduce a gap between the marker element and the bodily implant.

14. The bodily implant according to claim 1, further including at least one weld seam located at each of an inner circumference and an outer circumference of the marker element.

15. A bodily implant, comprising:
an implant structure having a cut-out formed therein; and
a marker element which is at least partially insertable into the cut-out in the implant structure, the marker element including a first layer and a second layer,
wherein the first layer has an X-ray visibility greater than an X-ray visibility of the second layer,
wherein the first layer and the second layer are each made of a material that is different than that of the implant structure and are each tapered such that the marker element is cone-shaped, and
wherein the first layer and the second layer each have side surfaces that contact the implant structure, the first layer and the second layer each have top and bottom surfaces, and the entire side surfaces of the first layer and the second layer are each tapered along a plane extending from the top surface of the second layer to the bottom surface of the first layer.

16. The bodily implant according to claim 15, wherein the first layer and the second layer are formed independent of the implant structure.

17. The bodily implant according to claim 15, wherein the second layer at least partially encapsulates the first layer.

18. The bodily implant according to claim 15, wherein each of the first layer and the second layer has a uniform thickness.

19. The bodily implant according to claim 18, wherein the thickness of the first layer is greater than the thickness of the second layer.

20. The bodily implant according to 19, wherein the marker element further includes a third layer, the first layer is disposed between the second layer and the third layer, and the third layer has the same thickness as the second layer.

21. The bodily implant according to claim 15, wherein the implant structure includes a top surface and a bottom surface, the cut-out extends from the top surface of the implant structure to the bottom surface of the implant structure, the cut-out is formed with angled surfaces relative to a plane bisecting the cut-out such that inner surfaces of the implant structure that extend from the top surface of the implant structure to the bottom surface of the implant structure and form the cut-out angle towards the plane when extending from the top surface of the implant structure to the bottom surface of the implant structure.

22. The bodily implant according to claim 21, wherein the side surfaces of the first layer and the second layer are each tapered at the same angle as the inner surfaces of the implant structure.

23. The bodily implant according to claim 21, wherein the marker element includes a third layer having a top surface and a bottom surface, the first layer is arranged between the second layer and the third layer, the bottom surface of the second layer contacts the top surface of the first layer, and the bottom surface of the first layer contacts the top surface of the third layer.

24. The bodily implant according to claim 23, wherein the marker element is shaped such that when the marker element is fully inserted into the cut-out in the implant structure, the top surface of the second layer is flush with the top surface of the implant structure and the bottom surface of the third layer is flush with the bottom surface of the implant structure.

25. The bodily implant according to claim 23, wherein the third layer further includes side surfaces, and the side surfaces of the first layer, the second layer, and the third layer are each tapered at the same angle as the inner surfaces of the implant structure.

26. The bodily implant according to claim 15, wherein the implant structure includes a top surface and a bottom surface, the cut-out extends only partially from the top surface of the implant structure to the bottom surface of the implant structure, the cut-out is formed with angled surfaces relative to a plane bisecting the cut-out such that inner surfaces of the implant structure that extend from the top surface of the implant structure to the bottom surface of the implant structure and form the cut-out angle towards the plane when extending from the top surface of the implant structure to the bottom surface of the implant structure.

27. The bodily implant according to claim 26, wherein the side surfaces of the first layer and the second layer are each tapered at the same angle as the inner surfaces of the implant structure.

28. The bodily implant according to claim 26, wherein the marker element is shaped such that when the marker element is fully inserted into the cut-out in the implant structure, the top surface of the first layer is flush with the top surface of the implant structure and the second layer is fully encapsulated by the first layer and the marker element.

29. A bodily implant, comprising:
an implant structure having a cut-out formed therein; and
a marker element to increase X-ray visibility which is at least partially insertable into the cut-out in the implant structure, the marker element including a first layer and a second layer,
wherein the first layer and the second layer are each tapered such that the marker element is cone-shaped, and
wherein the first layer and the second layer each have side surfaces that contact the implant structure, the first layer and the second layer each have top and bottom surfaces, and the entire side surfaces of the first layer and the second layer are each tapered along a plane extending from the top surface of the second layer to the bottom surface of the first layer.

30. The bodily implant according to claim 29, wherein the marker element further includes a third layer having a top surface and a bottom surface, the first layer being arranged between the second layer and the third layer such that the top surface of the first layer is in contact with the bottom surface of the second layer and the bottom surface of the first layer is in contact with the top surface of the third layer.

31. The bodily implant according to claim 30, wherein the third layer further has side surfaces, the plane extends from the top surface of the second layer through the bottom surface of the first layer to the bottom surface of the third layer, and the entire side surfaces of the first layer, the second layer, and the third layer are each tapered along the plane extending from the top surface of the second layer through the bottom surface of the first layer to the bottom surface of the third layer.

32. The bodily implant according to claim 31, further comprising at least one protective layer arranged between the implant structure and the side surfaces of each of the first layer, the second layer, and the third layer.

33. The bodily implant according to claim 30, wherein the first layer, the second layer, and the third layer are all curved relative to the plane extending from the top surface of the second layer to the bottom surface of the first layer.

34. The bodily implant according to claim 33, wherein the curvature of the first layer is the same as the curvature of the second layer which is the same as the curvature of the third layer.

35. The bodily implant according to claim 33, wherein a portion of the implant structure for receiving the marker element is curved and has a curvature equal to the curvature of the first layer, the second layer, and the third layer.

36. The bodily implant according to claim 29, wherein the first layer and the second layer are both curved relative to the plane extending from the top surface of the second layer to the bottom surface of the first layer.

37. The bodily implant according to claim 36, wherein the curvature of the first layer is the same as the curvature of the second layer.

38. The bodily implant according to claim 36, wherein the first layer has a uniform thickness, the second layer has a uniform thickness, and the uniform thickness of the first layer is greater than the uniform thickness of the second layer.

39. The bodily implant according to claim 36, wherein a portion of the implant structure for receiving the marker element is curved and has a curvature equal to the curvature of the first layer and the second layer.

40. The bodily implant according to claim 39, wherein the marker element and the cut-out are sized and shaped such that when the marker element is fully inserted into the implant structure, the top surface of the second layer is flush with a top surface of the implant structure.

41. The bodily implant according to claim 40, wherein the marker element and the cut-out are further sized and shaped such that when the marker element is fully inserted into the implant structure, the first layer is fully encapsulated by the second layer and the implant structure.

* * * * *